United States Patent [19]

Cook et al.

[11] Patent Number: 5,760,083
[45] Date of Patent: Jun. 2, 1998

[54] USE OF CLA TO REDUCE THE INCIDENCE OF VALGUS AND VARUS LEG DEFOROMITIES IN POULTRY

[75] Inventors: Mark E. Cook; Michael W. Pariza, both of Madison; Daria L. Jerome, Middleton, all of Wis.

[73] Assignee: Wisconsin Alumni Research Foundation, Madison, Wis.

[21] Appl. No.: 693,713

[22] Filed: Aug. 7, 1996

[51] Int. Cl.$^6$ .................... A61K 31/20
[52] U.S. Cl. .................... 514/560; 514/558
[58] Field of Search .................... 514/560, 558

[56] References Cited

U.S. PATENT DOCUMENTS

| | | | |
|---|---|---|---|
| 5,017,614 | 5/1991 | Pariza et al. | 514/558 |
| 5,070,104 | 12/1991 | Pariza et al. | 514/549 |
| 5,208,356 | 5/1993 | Pariza et al. | 554/79 |
| 5,428,072 | 6/1995 | Cook et al. | 514/560 |
| 5,430,066 | 7/1995 | Cook et al. | 514/558 |

OTHER PUBLICATIONS

Bruce A. Watkins, American Institute of Nutrition 1991 Symposium, pp. 1475–1485.

Bruce A. Watkins, American Institute of Nutrition 1993 Symposium, pp. 299–300.

Steven D. Bain and Bruce A. Watkins American Institute of Nutrition 1993 Symposium, pp. 317–322.

Bernhard Henning et al., American Institute of Nutrition, 1993 Symposium, pp. 1205–1216.

M. E. Cook, P. H. Patterson and M. L. Sunde, Poultry Science, 63:620–627 (1984).

M. E. Cook, W. T. Springer, K. M. Kerr and J. A. Hebert, Avian Diseases vol. 28, No. 5 (1984).

M. E. Cook, M. L. Sunde, J. L. Stahl and L. E. Hanson, Avian Diseases, vol. 28, No. 5 (1984).

P. H. Patterson, M. E. Cook, T. D. Crenshaw and Mr. L. Sunde, Poultry Science 65:1357–1364 (1986).

Tom Sullivan, Poultry Science 73:879–882 (1994).

M. E. Cook, Y. Bai, Poultry Science 73:889–896 (1994).

Michael S. Lilburn, Poultry Science 73:897–903 (1994).

Patricia Y. Hester, Poultry Science 73:904–915 91994).

R. M. Leach and W. O. Twal, Poultry Science 73:883–888 (1994).

*Primary Examiner*—Kevin E. Weddington
*Attorney, Agent, or Firm*—Quarles & Brady

[57] ABSTRACT

Methods of treating a bird to prevent skeletal problems consist of administering to the bird a safe and effective amount of CLA (conjugated linoleic acid).

10 Claims, No Drawings

USE OF CLA TO REDUCE THE INCIDENCE OF VALGUS AND VARUS LEG DEFOROMITIES IN POULTRY

FIELD OF THE INVENTION

The present application generally relates to methods of treating poultry. More particularly, it relates to methods of treating poultry to prevent skeletal problems, especially valgus and varus leg deformities i.e., twisted or bowed legs.

BACKGROUND OF THE INVENTION

Skeletal problems are recognized as one of the four major factors limiting the performance of meat-type birds. The fast-growing broilers and turkeys that reach market weights at earlier ages appear to have more leg problems and suffer greater losses than slower growing birds. There is survey data in the literature that indicates that the body weight of broilers is highly correlated to the severity of leg problems. The leading causes of leg problems in broilers include nutritional disorders, such as rickets; infectious diseases, such as viral arthritis, metabolic conditions, such as tibial dyschondroplasia; conformational problems, such as varus and valgus deformities; and toxins, such as mycotoxins.

Leg problems in broilers can increase mortality and increase the number of culls; they also can increase condemnations from septicemia-toxemia, and increase downgrades from trimming breasts and legs. In addition decreased feed consumption and increased disease also can occur.

It has been estimated that the annual losses due to leg problems in broilers is about $80 to $120 million. In turkeys, the cost estimates of annual production losses due to skeletal defects in the United States are as high as $32 million. Leg problems also cause losses for the growers of other birds, such as pheasants, emus, ostriches, rhea and other ratites.

Obviously, it would be advantageous to have methods of treating poultry to prevent skeletal deformities, especially leg deformities.

BRIEF SUMMARY OF THE INVENTION

It is the object of the present invention to disclose a method of preventing skeletal problems in poultry.

We have discovered a method of preventing skeletal problems in poultry which comprises administering to a bird susceptible to skeletal problems a safe and effective amount of a conjugated linoleic acid, such as 9,11-octadecadienoic acid and 10,12-octadecadienoic acid, a non-toxic salt of a conjugated linoleic acid, an active ester of a conjugated linoleic acid, active isomers, active metabolites or a mixture thereof.

The conjugated linoleic acids, their non-toxic salts, active esters, active isomers, active metabolites, and mixtures thereof are referred to herein as "CLA".

It will be apparent to those skilled in the art that the forementioned objects and other advantages may be achieved by the practice of the present invention.

DESCRIPTION OF THE PREFERRED EMBODIMENT

In the preferred method of the present invention, CLA is orally administered to a bird in a safe amount which is effective to prevent skeletal problems, especially leg deformities. Because of the differences in ages, size and nature of birds, the amounts which are safe and effective may vary considerably. Since CLA is a natural food ingredient and it is relatively non-toxic, the amounts which can be administered in the methods of the invention are not critical as long as they are enough to be effective.

The practice of the present invention is further illustrated by the examples which follow:

EXAMPLE 1

Six pens of 5 chicks were fed CLA at 0,0.1875, 0.375, and 0.75% of the diet. At 3 weeks of age the legs of the chicks were scored for twisted, bowed condition. Scoring was 1=normal, 2=slight, 3=moderate, and 4=severe (essentially crippled). The results after 3 weeks are shown in Table 1.

TABLE 1

| CLA Content | Body Weight (g) | Mean Leg Score Mean ± Std Error | Percent with Severe bending |
|---|---|---|---|
| 0% | 605 | 2.0 ± 0.2 | 27 ± 7* |
| 0.1875% | 606 | 1.7 ± 0.2 | 13 ± 10 |
| 0.375% | 618 | 1.6 ± 0.4 | 7 ± 4 |
| 0.75% | 601 | 1.4 ± 0.2 | 3 ± 3* |

Table 2 shows the results obtained after 8 weeks in 10 control birds and the 10 birds fed the diet containing 0.75% CLA.

TABLE 2

| CLA Content | Body Weight (g) | Mean Leg Score Mean ± Std Error | Percent with Severe bending |
|---|---|---|---|
| 0% | 2372 | 2.2 | 33 |
| 0.75% | 2745 | 1.1 | 0 |

*Only 1 of 30 chicks had severe score in high CLA, with 8 out of 30 in control.

After 9 weeks the control birds had an average body weight of 2684 g and the birds receiving. CLA had an average body weight of 3220 g.

As can be seen from the above, the birds fed the 0.75% CLA diet gained significantly more weight than the control birds. Similar results can be obtained in turkeys, ducks, geese, emus, pheasants, ostriches, rheas and other ratites.

The method of the present invention may take several embodiments. In one embodiment, the CLA is added to a bird's diet by adding the CLA to poultry feed. In another embodiment, the CLA can be administered to the bird in a veterinary composition containing a safe and effective dose. of the CLA. In still another embodiment, the bird is fed a food product, such as milk or egg solids, which have been enriched so that they contain high concentrations of CLA.

The poultry feed and veterinary preparations for use in the methods of the present invention preferably are those containing the CLA in the form of the triglyceride esters in combination with a conventional poultry feed or approved veterinary diluent. Other active forms of CLA including, without limitation, the non-toxic salts and mixtures can be used.

The free conjugated linoleic acids (CLA) have been previously isolated from fried meats and described as anti-carcinogens by Y. L. Ha, N. K. Grimm and M. W. Pariza, in *Carcinogenesis* Vol. 8, No. 12, pp. 1881–1887 (1987). Since then, they have been found in some processed cheese products (Y. L. Ha, N. K. Grimm and M. W. Pariza, in *J. Agric. Food Chem.*, Vol. 37, No. 1, pp. 75–81 (1987)).

The free acid forms of the CLA may be prepared by isomerizing linoleic acid. The non-toxic salts of the free CLA acids may be made by reacting the free acids with a non-toxic base. Natural CLA may also be prepared from linoleic acid by the action of $W^{12}$-cis, $W^{11}$-transisomerase from a harmless microorganism such as the Rumen bacterium *Butyrivibrio fibrisolvens*. Harmless microorganisms in the intestinal tracts of rats and other monogastric animals may also convert linoleic acid to CLA (S. F. Chin, W. Liu, K. Albright and M. W. Pariza, 1992, FASEB J.6:Abstract #2665).

The CLA obtained by the practice of the described methods of preparation contains one or more of the 9,11-octadecadienoic acids and/or 10,12-octadecadienoic acids and active isomers thereof. It may be free or bound chemically through ester linkages. The CLA is heat stable and can be used as is, or dried and powdered. The free acids are readily converted into non-toxic salts, such as the sodium or potassium salts, by reacting chemically equivalent amounts of the free acid with an alkali hydroxide at a pH of about 8 to 9.

Theoretically, 8 possible geometric isomers of 9,11-and 10,12-octadecadienoic acid (c9,c11; c9,t11; t9,c11; t9,t11; c10,c12; c10,t12; t10,c12 and t10,t12) would form from the isomerization of c9,c12-octadecadienoic acid. As a result of the isomerization, only four isomers (c9,c11; c9,t11; t10, c12; and c10,c12) would be expected. However, of the four isomers, c9,t11- and t10,c12- isomers are predominantly produced during the autoxidation or alkali-isomerization of c9,c12-linoleic acid due to the co-planar characteristics of 5 carbon atoms around a conjugated double-bond and spatial conflict of the resonance radical. The remaining two c,c-isomers are minor contributors.

The relatively higher distribution of the t,t-isomers of 9,11- or 10,12-octadecadienoic acid apparently results from the further stabilization of c9,t11- or t10,c12-geometric isomers, which is thermodynamically preferred, during an extended processing time or long aging period. Additionally the t,t-isomer of 9,11- or 10,12-octadecadienoic acid that was predominantly formed during the isomerization of linoleic acid geometrical isomers (t9,t12-, c9,t12- and t9,c12-octadecadienoic acid) may influence the final ratio of the isomers or the final CLA content in the samples.

Linoleic acid geometrical isomers also influence the distribution of minor contributors (c,c-isomers of 9,11- and 10,12-, t9,c11- and c11,t12-octadecadienoic acids). The 11,13-isomer might be produced as a minor product from c9,c12-octadecadienoic acid or from its isomeric forms during processing.

The CLA can be administered in the form of veterinary compositions, such as solutions or emulsions. The exact amount to be administered, of course, depends upon the form of CLA employed, and the route of administration. Generally, the amount employed of the non-toxic salts in a veterinary composition will range from about one part per million (ppm) to about 10,000 ppm of CLA of the bird's diet.

The preferred veterinary compositions of CLA contain the non-toxic sodium or potassium salt of CLA in combination with a suitable diluent. In addition to solutions or suspensions intended for oral administration the product can be a powder or a crushable tablet. When the compositions are solutions or suspensions intended for parenteral administration the preferred diluent will be Sterile Water for Injection U.S.P.

The amounts of CLA to be added to poultry feed can range from about 0.01% to about 5.0% or more by weight of the bird's diet. The bird can be fed a diet containing the CLA from birth to harvesting or for some other period until at least some of beneficial effects of the CLA are obtained.

It will be readily apparent to those skilled in the art that a number of modifications or changes may be made without departing from the spirit and scope of the present invention. Therefore, the invention is only to be limited by the claims.

We claim:

1. A method of preventing skeletal problems in a bird predisposed to developing skeletal problems, said method comprising administering to said bird a safe amount of CLA which is effective to prevent skeletal problems.

2. The method of claim 1 in which the CLA is a non-toxic salt of a conjugated linoleic acid.

3. The method of claim 1 in which the CLA is a triglyceride of a conjugated linoleic acid.

4. The method of claim 1 in which the bird is a chicken.

5. The method of claim 1 in which the bird is a turkey.

6. The method of claim 1 in which the bird is a duck.

7. The method of claim 1 in which the CLA is administered orally.

8. The method of claim 1 in which the CLA is administered parenterally.

9. The method of claim 1 in which the skeletal problems are leg deformities.

10. A method of improving growth and feed efficiency in birds and reducing losses due to culls, condemnation and mortality caused by leg problems, the method comprising administering to said birds a safe amount of CLA which is effective to prevent leg deformities and other skeletal problems.

* * * * *